United States Patent [19]

Gombrich et al.

[11] 4,083,366

[45] Apr. 11, 1978

[54] HEART BEAT RATE MONITOR

[75] Inventor: Peter P. Gombrich,
416 N. Westwood Dr.,
Golden Valley, Minn. 55422;
Michael L. Harvey,
Ewa Beach, Hi.

[73] Assignee: Peter P. Gombrich, Golden Valley, Minn.

[21] Appl. No.: 696,497

[22] Filed: Jun. 16, 1976

[51] Int. Cl.² ............................................. A61B 5/02
[52] U.S. Cl. ............................................. 128/2.05 T
[58] Field of Search ............ 128/2.05 P, 2.05 R,
128/2.05 T, 2.06 A, 2.06 F, 2.06 R

[56] References Cited

U.S. PATENT DOCUMENTS

| | | | |
|---|---|---|---|
| 3,612,041 | 10/1971 | Ragsdale | 128/2.06 A |
| 3,633,569 | 1/1972 | Brayshaw et al. | 128/2.06 A |
| 3,727,616 | 4/1973 | Lenzkes | 128/419 E X |
| 3,802,698 | 4/1974 | Burian et al. | 128/2.06 F X |
| 3,833,005 | 9/1974 | Wingrove | 128/419 PG |
| 3,908,636 | 9/1975 | Page | 128/2.05 T |
| 3,948,250 | 4/1976 | Weisman | 128/2.06 F |
| 3,978,849 | 9/1976 | Geneen | 128/2.05 T |

Primary Examiner—William E. Kamm
Attorney, Agent, or Firm—Lindenberg, Freilich, Hornbaker, Wasserman, Rosen & Fernandez

[57] ABSTRACT

A heart beat rate monitor is provided with memory means for storing upper and lower limits of a range of heart beat rates. The limits are transmitted to and stored in the memory from an external source. The monitor wearer's heart beat is sensed and whenever the sensed beat rate is outside the range defined by the limits an out-of-range indication is provided to the wearer. The memory means are powered so as not to be affected by the depletion of the main battery which is the primary source of power for the monitor circuitry. In some embodiments, the limits received from the external unit are transmitted thereto for verification purposes. In some embodiments the actual sensed heart beat rate and/or the stored limits are displayable to the wearer upon request.

31 Claims, 11 Drawing Figures

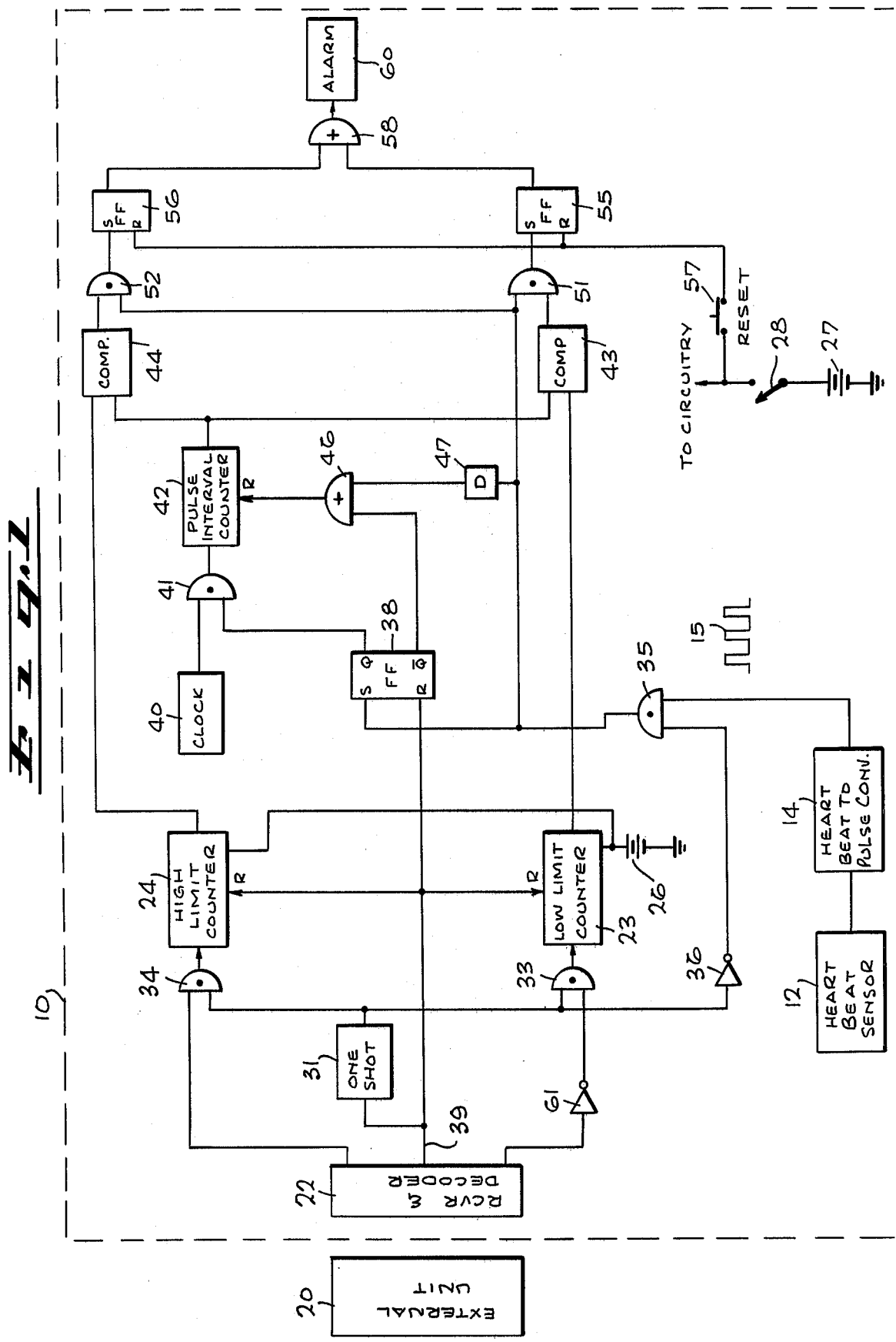

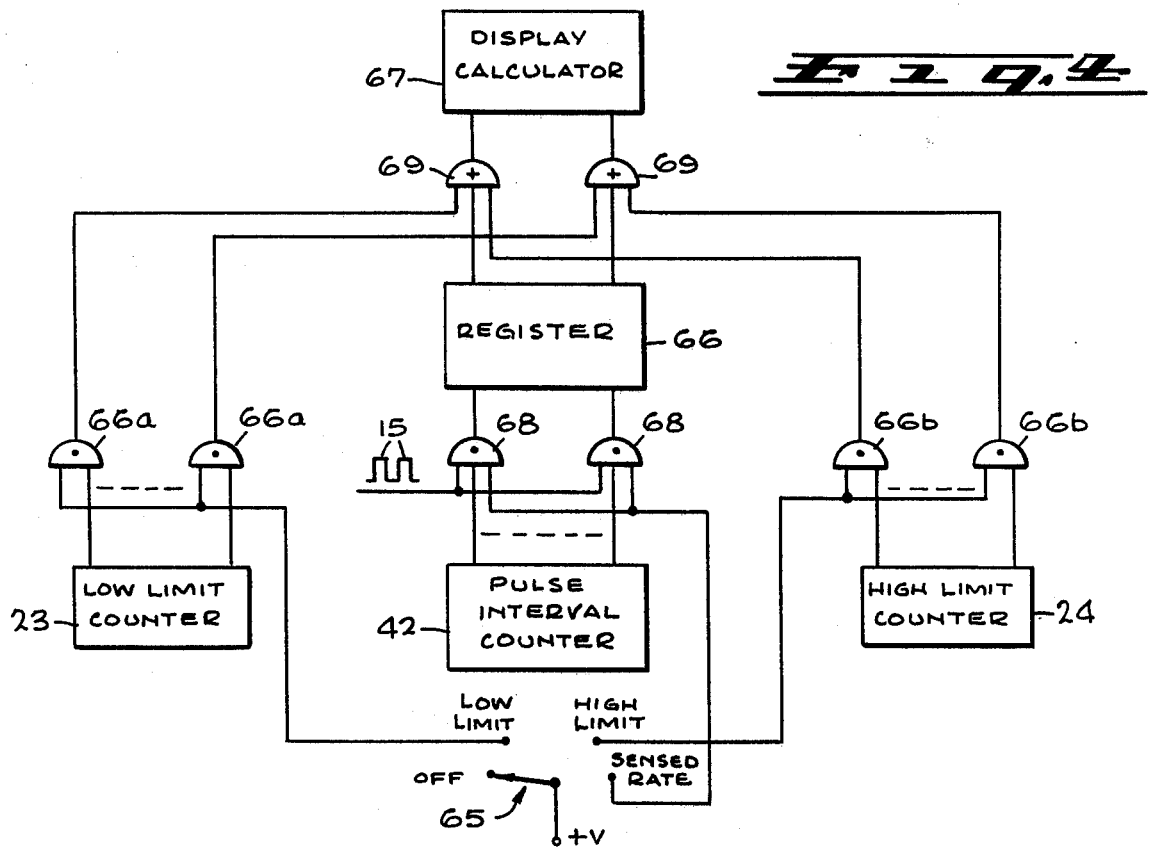
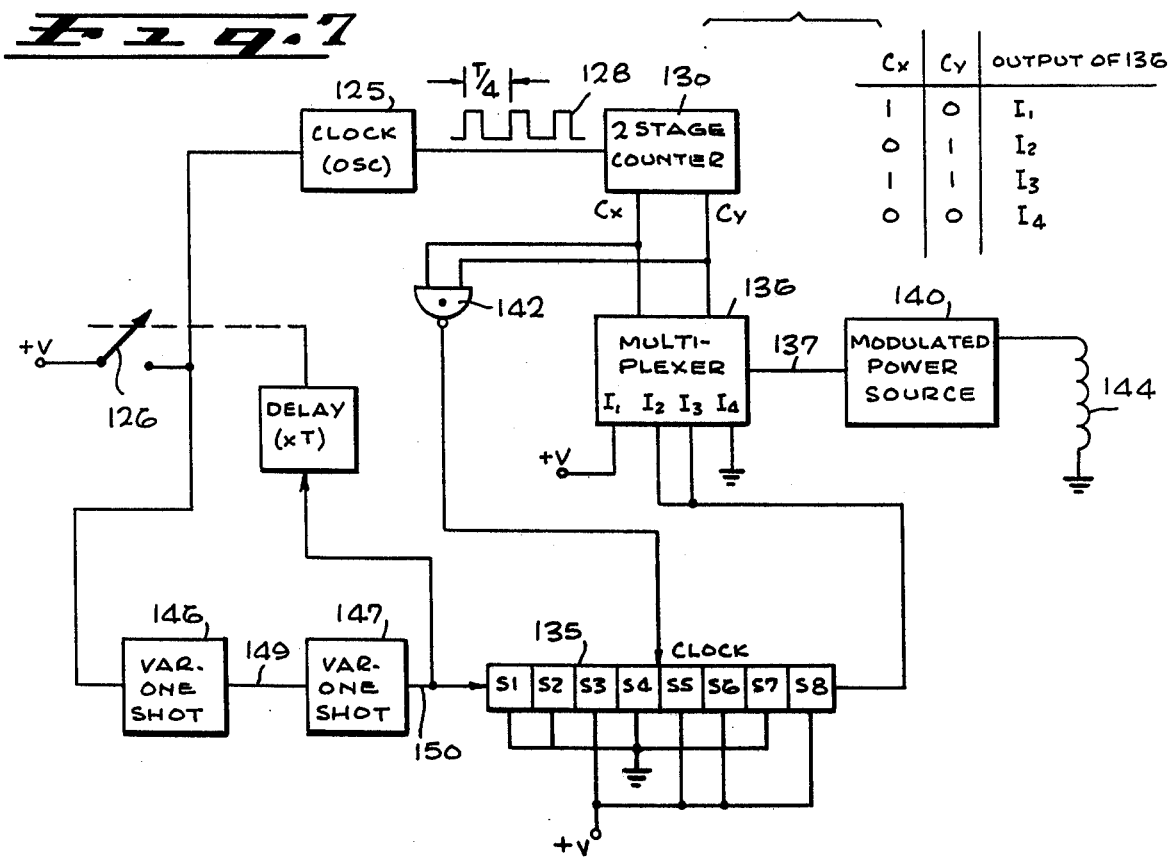

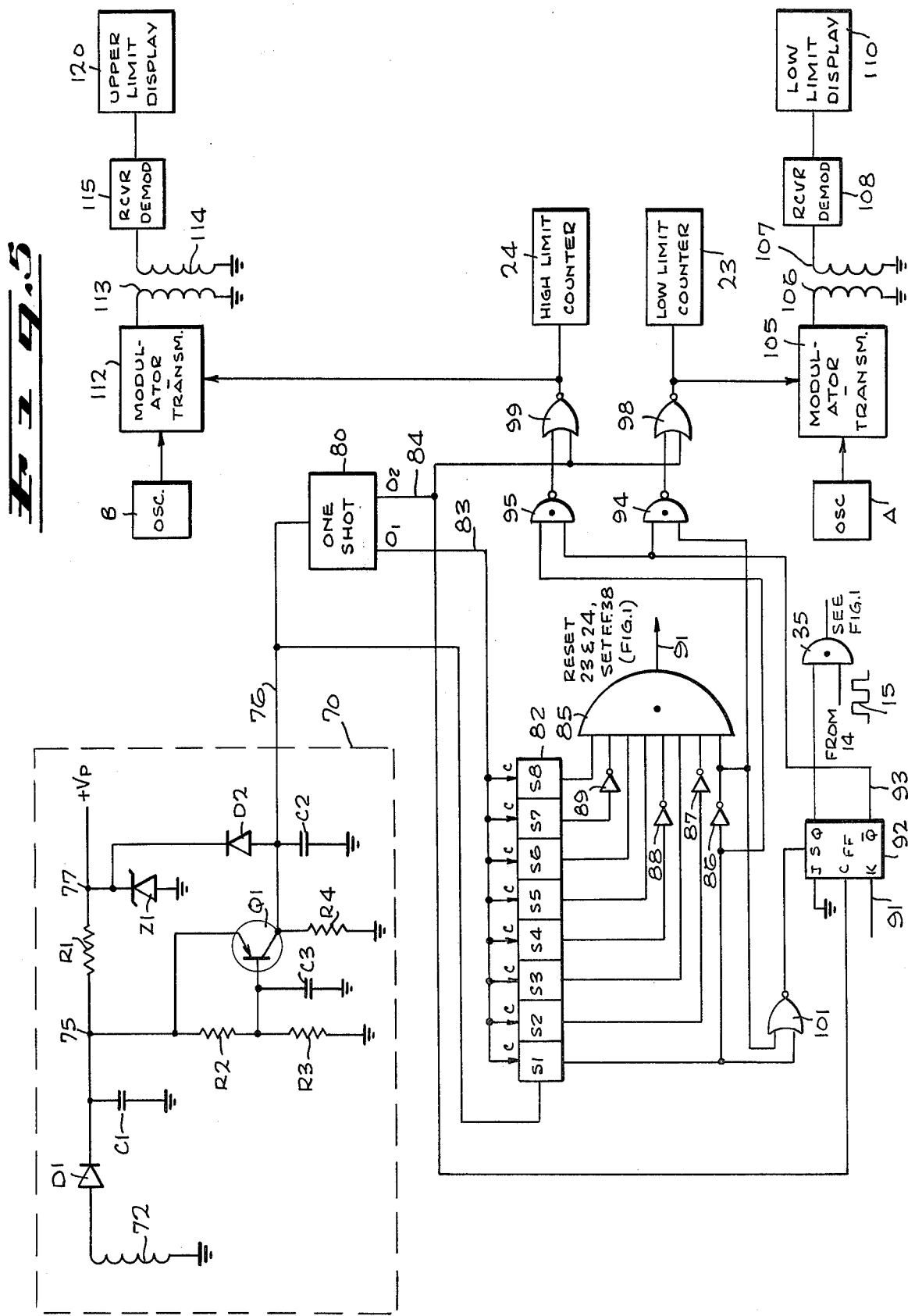

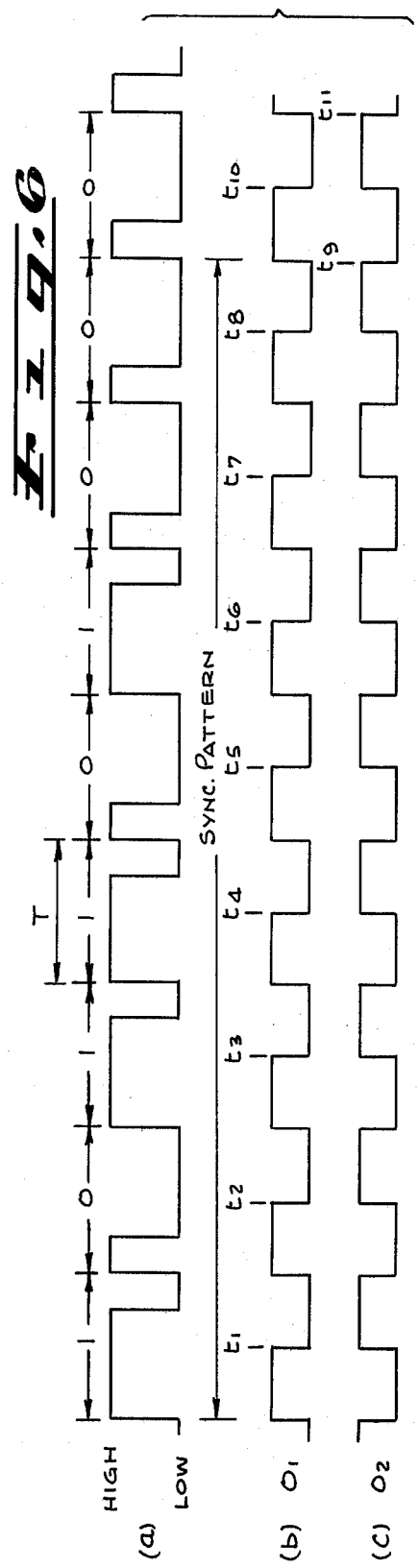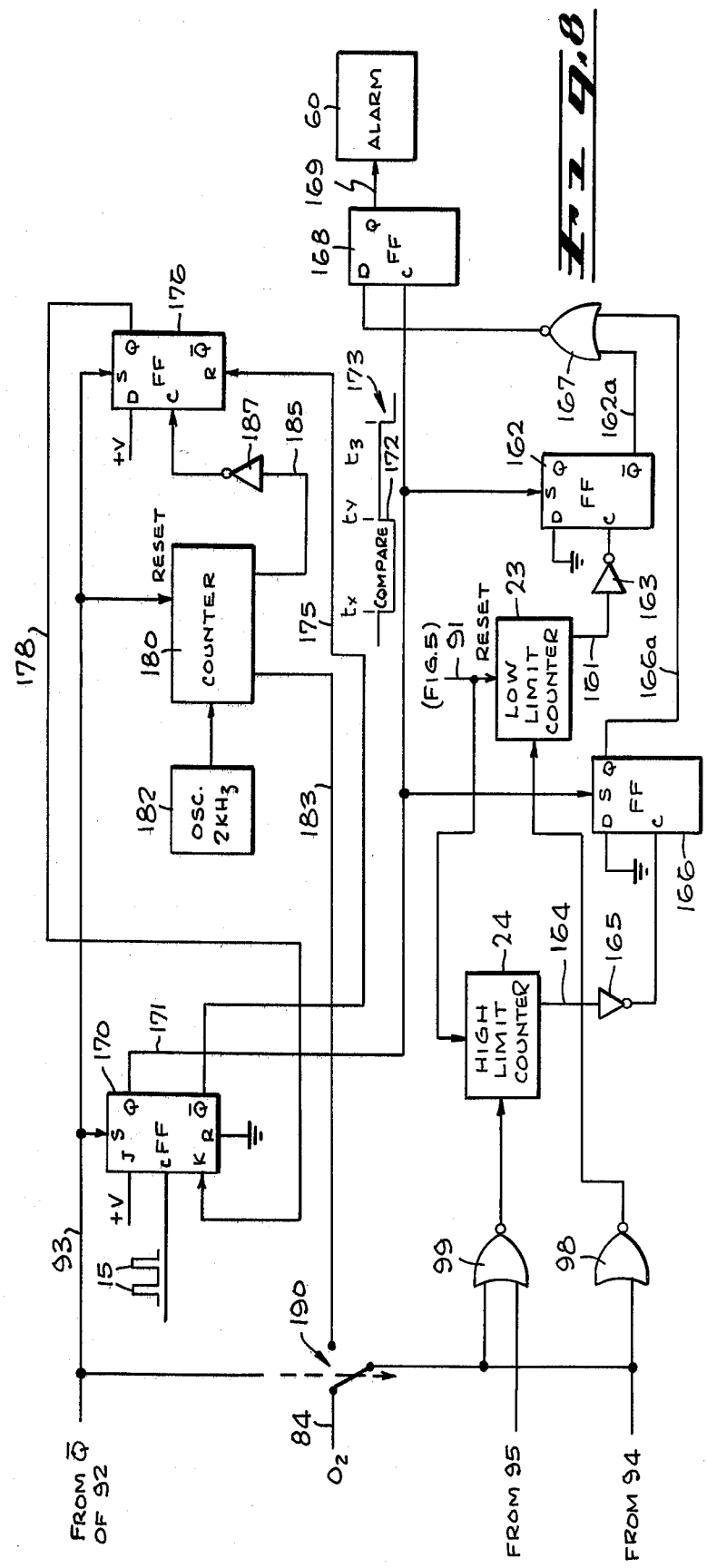

HEART BEAT RATE MONITOR

BACKGROUND OF THE INVENTION

1. Field of the Invention

The present invention generally relates to a pulse rate monitor and, more particularly, to a device for monitoring the rate of human heart beating and for providing an indication when the heart beats at a rate which is outside a rate range, defined by limits, which are programmable into the device from an external source.

2. Description of the Prior Art

As is appreciated, during each systolic heart beat the heart contracts, forcing blood through the arteries, in the course of which the arteries expand. This expansion can be sensed either manually or by means of sensing devices at various points in the body. Typically, it is sensed at the wrist, or at the carotid artery at the neck. Various devices have been proposed in the prior art to measure or monitor the human body heart beat rate, which is generally expressed in terms of beats or pulses per minute.

In the devices, proposed to measure the heart beat rate, various means have been proposed to automatically sense the heart beats by sensing the expanding arteries. These means include pressure transducers, photoelectric devices, mechanical diaphragms and the like. The sensed heart beats are typically converted into corresponding electrical pulses whose rate is monitored. Some presently known heart beat monitors provide an indication whenever the heart beat rate is outside a rate defined by high and low rate limits, which are manually set in the monitor.

The use of a heart beat monitor, capable of providing an indication when the heart beat rate exceeds and/or falls below selected rate limits is particularly important for a patient having questionable cardiac conditions, e.g., a patient with a cardiac stimulator. By presetting the heart beat monitor with high and low rate limits, chosen to be above and below the patient's pacemaker pulse rate, or the patient's normal pulse rate, the heart beat monitor can be used to indicate pacemaker failure or excessive pulse rate above a normal rate.

The heart beat monitor, particularly one with a preset upper limit can be used very effectively for post heart attack patients. Generally, doctors advise such patients to exercise in order to strengthen their heart muscles. However, when exercising it is most important that the weakened heart muscles not be overtaxed. This can be achieved by first setting the high or upper limit in the heart beat monitor to a selected relatively low level, and permit the patient to first exercise until his heart beat rate reaches the set limit. Then, as the patient's condition improves the upper limit may be raised. Since practically all post heart attack patients are under a doctor's care, it is of primary importance to enable the doctor, rather than the patient, to establish the limits in the heart beat monitor, based on the medical diagnosis of the patient's conditions.

In the prior art, heart beat monitors have been described which are in the form of a wristwatch intended to be worn by the patient. Some of these monitors include means which enable the patient to set and vary the upper and lower limits by manipulating dials or other means in the monitor. This is, the limits are subject to change by the patient rather than the doctor, and therefore may be set at unsafe levels for the particular patient condition. A need therefore exists for a heart beat monitor in which the limits are programmable or storeable into the monitor from an external source under the control of a doctor or the like. Once the limits are stored they should not be subject to variation by the monitor-wearing patient, except by a subsequent programming operation, from the external source. Such a monitor would prevent the patient from setting improper limits in the monitor.

In such an externally programmable monitor it is highly desirable to store the limits so that they remain unaffected by the monitor's main power source, e.g., a primary battery, which may be depleted by energization of the various monitor circuits including an audible alarm and/or a visual rate display.

OBJECTS AND SUMMARY OF THE INVENTION

It is a primay object of the invention to provide a new heart beat monitor.

Another object of the invention is to provide a new heart beat monitor, into which upper and/or lower rate limits are programmed and stored from a source external to the monitor, so that the limits cannot be varied except by a subsequent programming and storing operation.

A further object of the present invention is to provide a new lightweight heart beat monitor designed to receive and store only preselected rate limits which are transmitted thereto from an external source, and to provide one or more indications whenever the heart beat rate is outside a range defined by said limits.

These and other objects of the invention are achieved by providing a heart beat monitor which includes means for sensing the heart beats and comparing their rate with ratedefining limits, stored in a memory section thereof. The monitor further includes means for providing one or more indications whenever the rate of the sensed heart beats is in a range outside one defined by the rate limits stored in the memory. The novel monitor includes telemetry receiver and decoder means, designed to receive rate-limit-indicating signals, which are transmitted thereto from an external source. These rate-limit-indicating signals are used to store rate limits corresponding thereto in the memory means. It is these rate limits which define a heart beat rate range, so that when the sensed rate of the heart beat is outside their limits an indication is provided to the patient.

To immunize the system from noise and from undesired sources of signals which may be mistaken for rate-limit-indicating signals, the transmission of appropriate rate-limit indicating signals takes place only after the transmission of a preselected code, hereinafter referred to as a sync pattern. Only when the latter is received and decoded are ths subsequently received rate-limit-indicating signals used to store the limits indicated thereby in the memory means. To further increase system reliability it is important to protect the memory means from being affected by the depletion of the main power source which is used to energize the rest of the monitor circuitry, including the means used to provide the indication(s) when the heart beat rate is outside the limits' defining range. This may be achieved by powering the memory means with a power source, e.g., a battery which is separate from the main power source. Alternately, a single power source may be used and a voltage sensor may be incorporated to disable all the circuitry, except the memory means, from the single power source when the sensed voltage drops below a safe level. Limits in the memory means can only be changed the the reception of a different set of rate-limit-indicating signals which follow the preselected code. In some embodiments means are included to display the monitor wearer his actual heart beat rate. Also, in some embodiments means are provided to retransmit signals to the external source, indicating the limits received from the latter for verification purposes. Furthermore, in some embodiments means are provided within the monitor to display, upon the request the limits stored therein.

The novel features of the invention are set forth with particularity in the appended claims. The invention will best be understood from the following description when read in conjunction with the accompanying drawings.

BRIEF DESCRIPTION OF THE DRAWINGS

FIG. 1 is a block diagram of one embodiment of the monitor of the present invention;

FIG. 4 is a diagram of monitor circuitry for selectively displaying sensed heart rate, a stored rate low limit or a rate high limit;

FIG. 5 is a diagram of a receiver-decoder unit 22, shown in FIG. 1 and means for retransmitting rate-limit-indicating signals which were received from an external unit to the latter;

FIG. 6 is a multiline waveform diagram useful in explaining the operation of circuitry shown in FIG. 5;

FIG. 7 is diagram of one embodiment of an external unit 20;

FIG. 8 is a partial diagram of another embodiment of monitor circuitry;

DESCRIPTION OF THE PREFERRED EMBODIMENTS

Figure 1A:
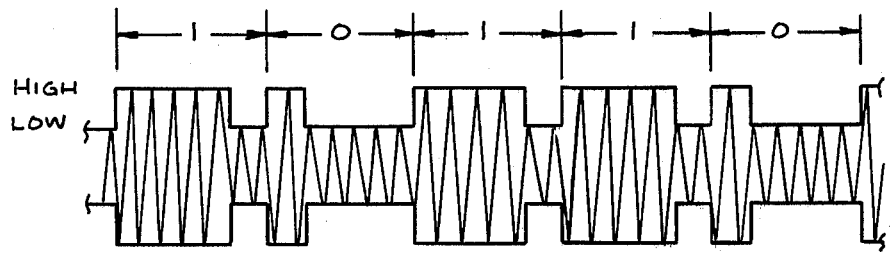
FIG. 1a is a waveform diagram of a binary modulated RF carrier useful in explaining one aspect of the invention.

Attention is now directed to FIG. 1 in connection with which an embodiment, useful in explaining the basic principles and advantages of the present invention, will be described. Thereafter, different embodiments will be described. As previously pointed out, in accordance with the present invention rate limits are stored in the memory means of the monitor. These rates limits define a heart beat range, so that when the sensed heart beat rate is outside the range an indication is provided to the monitor wearer. These limits are transmitted to the monitor for storage therein from an external transmitter unit in the from of rate-limit-indicating signals. In order to insure that the rate limits correspond only to appropriately transmitted rate-limit-indicating signals and are not affected by noise or other spurious signal sources, a selected code, hereinafter referred to as a sync pattern, is transmitted ahead of the rate-limit-indicating signals. Thus, only when the sync pattern is received and identified are the subsequently received rate-limit-indicating signals used to store the rate limits. Otherwise, the previously stored rate limits remain unaffected.

Preferably, the memory means are powered by a power source, e.g., a battery which is separate from the main battery, which is used to power the rest of the monitor circuitry. In such an arrangement the long term, low current drain of the main battery by the memory means is eliminated. Also, when the main battery runs down and has to be replaced, the memory content is not lost. In a preferred embodiment, means are incorporated to transmit signals to the external unit to verify that the previously transmitted signals from the external unit resulted in the storage of proper rate limits. Also, to reduce drainage of the battery or batteries of the monitor, if desired, the power receive during the reception of the sync pattern and the following rate-limit-indicating signals may be used to provide power for the circuitry which is used to decode and identify the sync pattern and feed the following signals to the memory means.

In FIG. 1, numeral 10 designates a heart beat monitor which is assumed to be of the wrist type, i.e., one to be worn on the wrist, like a watch. It includes heart beat sensor 12 which senses the heart beats. Any of the presently known devices capable of sensing heart bearts may be used. For example, sensor 12 may be in the form of an electrode, such as is used in recording EKGs, or a strain gauge or mechanical diaphragm, designed to sense external skin motion which varies due to the blood flow rate. Also, it may be a ultrasonic doppler type sensor. In general, sensor 12 may be any known device capable of sensing heart beats. As shown in FIG. 1, the output of sensor 12 is connected to a beat-to-pulse converter 14 whose output is a sequence of beat pulses 15, each pulse corresponding to one heart beat. It is the rate of these pulses that the monitor 10 is designed to monitor and indicate when their rate is outside a selected range.

The limits of the range are supplied to the monitor 10 from an external unit 20. The latter is assumed to include circuitry, such as knobs, or dials, by means of which an operator, e.g., a physician, can set the desired limits to be transmitted. After selecting the range limit a transmit switch is activated. As a result, a preselected fixed sync pattern is generated and is followed by a first sequence of pulses which represents one of the range limits, e.g., the lower or low limit and a second sequence of pulses representing the upper or high limit. Binary techniques are employed so that the sync pattern is a selected pattern of a fixed number of bits. For explanatory purposes let it be assumed that the sync pattern is an eightbit pattern such as 00101101 as viewed from right to left. It is further assumed that is followed by a number of 0's which define the selected low limit and by a numer of 1's which define the high limit. A 0 following the last 1 indicates the end of the complete sequence. The number of 0's defining the low limit and the number of 1's defining the high limit, depend on the limits selected by the operator.

Generally, the sequence with the sync pattern viewed from right to left may be represented by

| end bit | 01 | ..... | 10 | ..... | 00101101 |
|---|---|---|---|---|---|
| | | high limit | | low limit | sync pattern |

This bit sequence is used in the external unit 20 to modulate an RF carrier signal, whose modulated output, e.g., amplitude modulated is transmitted via a transmitter coil to a receiver and demodulator unit 22 of monitor 10.

In unit 22 the received RF carrier is demodulated and decoded to retrieve the original modulating binary sequence. The unit 22 includes an 8-bit sync pattern decoder. Upon sensing the proper 8-bit sync pattern of 00101101 it enables the following sequence of 0's representing the selected low limit, to be stored in a low limit counter 23. Then, the following sequences of 1's representing the high limit, are stored in a high limit counter 24. Once the 0 end bit is sensed it effecitvely disables the unit 22 from supplying additional limit-indicating signals to the counters. Thus, the proper limits are stored in the counters 23 and 24 and they remain stored therein, without being altered, until it is desired to change the limits. This is achievable by transmitting another bit sequence which includes the proper sync pattern as the front or leading portion of the sequence.

The RF carrier power is chosen to be high enough to enable unit 22 which may be located at a selected distance, e.g., several inches, from the external unit 20 to receive the transmitted signal. In unit 22 the transmitted waveform is received by appropriate means, e.g., a pickup coil, and is demodulated to extract the waveform-modulating binary sequence. It should be appreciated that the various circuit arrangements and techniques, well known by those familiar with the art, may be used for this end. The transmitted power should be sufficiently low so as not to provide RF interference which would require FCC certification. It should be apparent that different frequencies and techniques may be used to transmit a binary sequence as hereinbefore described to the monitor. For example, the carrier frequency may be above the audio range, e.g., 22KHz, with 30–50% amplitude modulation. The sequence may be transmitted at any desired bit range, e.g., 200 bits per second. Defining each bit period as T, a logical 1 may be in the form of $\frac{3}{4}$T On and $\frac{1}{4}$T Off, while a logical 0 may be $\frac{1}{4}$T On and $\frac{3}{4}$T Off. An example of such a modulated waveform is shown in FIG. 1a, for the first 5 bits 10110 of the sync patern, as viewed from left to right. "On" refers to a high level and "Off" to a low level.

In order not to distrub the limits which are stored in the counters 23 and 24, which together represent memory means, as previously pointed out, it is preferably to power these counters with a battery 26, which is separate from a main battery 27, used to power the rest of the monitor's circuitry. Thus, the depletion of the main battery 27 does not affect the contents of the counters 23 and 24. In FIG. 1, numeral 28 represents a manually operable On-Off switch (shown in the Off position) which the wearer may turn On only when wearing the monitor and thereby minimize the drainage of main battery 27 when the monitor is not in use. Switch 28 is preferably of the type which is switched On when the monitor is worn by the wearer and is switched Off when the monitor is removed. For example, it may be a very small pushbutton type switch on the back of the monitor which is automatically pushed to be in the On position when the wrist monitor is placed on the wrist.

In the embodiment, diagrammed in FIG. 1, the monitor is shown including a one shot 31 which is used to control input And gates 33 nd 34 of counters 23 and 24, respectively. Also, shown is an And gate 35, having one input which receives the beat pulses 15 from converter 14 and another input, connected to one short 31 through an inverter 36. Also included is a control flip flop (FF) 38 with its set (S) input controlled by gate 35 and its reset (R) input connected to a line 39 at which a control level, assumed to be high, is applied only when the sync pattern is first recognized by unit 22.

The $\bar{Q}$ output of FF 38 is connected to one input of an And gate 41, whose other input is connected to a clock 40. The output of gate 41 clocks a pulse interval counter 42, whose output is supplied to each of comparators 43 and 44. Counter 42 is resettable by the output of an Or gate 46. The latter is supplied with the $\bar{Q}$ output of FF 38, and with the output of gate 35 through a delay unit 47. The output of gate 35 is also applied directly to one input of each of And gates 51 and 52. The former is also supplied with the output of comparator 43 while gate 52 is supplied with the output of comparator 44.

The outputs of gates 51 and 52 are respectively connected to the set (S) inputs of flip flops 55 and 56, whose reset (R) inputs are connected through a reset switch 57 to the battery 27, when switch 28 is closed (On). The Q outputs of FFs 55 and 56 are connected to an Or gate 58 whose output is connected to an alarm 60. The alarm is activated only when enabled by gate 58 which occurs whenever either FF 55 or FF 56 is set.

Figure 2:
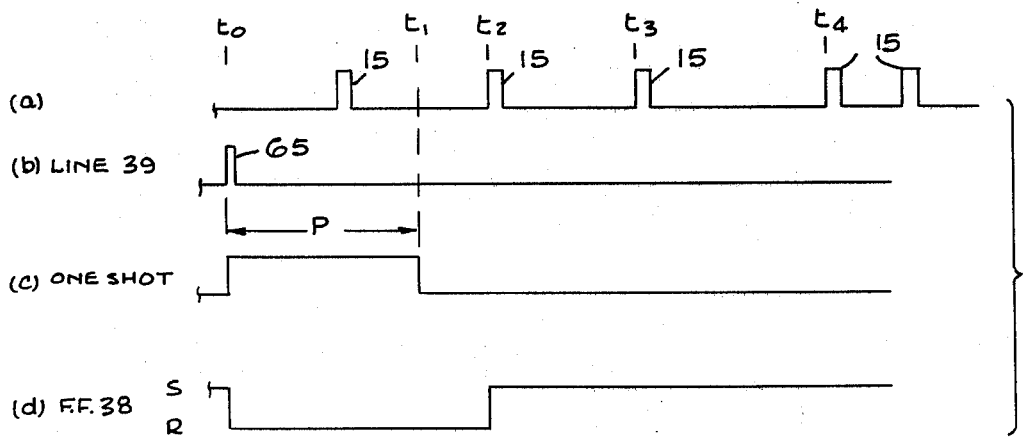
FIG. 2 is a multiwaveform diagram useful in explaining the operation of the circuitry shown in FIG. 1.

The operation of the monitor 10 may best be described in connection with a specific example and the multi-line waveform diagram shown in FIG. 2. For explanatory purposes let it be assumed that clock 40 provides 100 pulses per second (pps) and that the desired heart beat range to be monitored is between 60 beats per minute (bpm) and 120 bpm, which correspond to 1 beat per second (bps) and 2bps. For this particular example, the bit sequence may include 100 0's to define the low limit of 1 bps, and 50 1's to define the high limit. In FIG. 2, lines $a$–$d$ are used to diagram the waveforms of beat pulses 15, the level on line 39, the output of one shot 31 and the state of FF 38, respectively.

Let it be assumed that at time $t_0$ unit 22 detects the sync pattern. Thus, line 39 goes high, as represented by pulse 65 (line $b$), for the bit duration between the last sync pattern and the first 0 of the sequence defining the low limit. When line 39 goes high, it resets FF 38 (line $d$). Consequently, gate 41 is disabled to prevent the pulses from clock 40 to be clocked into counter 42. The latter is reset through Or gate 46 since the $\bar{Q}$ output of FF 38 is high. Also, when line 39 goes high it resets counters 23 and 24 to an all zero count. In addition, it activates one shot 31 whose output goes high (line $c$) thereby enabling gates 33 nd 34. The 0's defining the low limit, from unit 22 are inverted into 1's by an inverter 61 and are clocked into counter 23 through enabled gate 33. In the particular example 100 pulses are clocked into counter 23. The subsequent sequence of 1's defining the high limit, passes from the unit 22 through gate 34 and are clocked or counted in counter 24. For the specific example 50 pulses are counted.

The period P, during which the output of one shot 31 is high, is chosen to be long enough to insure that both the 0 and 1 sequences, which define the limits are clocked into the two counters 23 and 24. With modern binary signal transmission techniques, transmission rates of thousands of bits per second is easily achievable. Thus, the limit-defining 0's and 1's can be loaded into their respective counters in a fraction of a second. Therefore, the period P can be less than one second. However, in any case it has to be long enough to maintain gates 33 and 34 open until the two limit-defining sequences are used to store the limits in the two counters.

It should be noted that as long as the output of one shot 31 is high the output of inverter 36 is low. Therefore, gate 35 is disabled and consequently beat pulses 15 do not pass beyond gate 35. At the end of the period P, at time $t_1$, the output of one shot 31 goes low, thereby disabling gates 33 and 34, and the output of inverter 36 goes high. Following $t_1$ when the next beat pulse 15 is received, such as at $t_2$, the output of gate 35 goes high, setting FF 38 (line $d$). Therefore, its Q output goes high and thereby enables gate 41, to enable the pulses from clock 40 to be clocked or counted in counter 42. These pulses are assumed to be at a rate of 100 pps. Once FF 38 is set it remains set until a subsequent sync pattern is recognized and line 39 goes high.

Until the next beat pulse 15 is received such as at time $t_3$ the counter 42 is clocked by the pulses from clock 40 at the rate of 100 pps. Also, comparator 43 compares the count in counter 42 with the count of 100 (for 1 bps), stored in low limit counter 23. Similarly, comparator 44 compares the count of 50 (for 2 bps) in counter 24 with the count in counter 42. Comparator 43 operates to provide a high output only when the count in counter 42 is greater than that in counter 23. Otherwise, the output of comparator 43 is low. On the other hand comparator 44 operates to provide a high output only when the count in counter 42 is less than that in counter 24. Otherwise, the output of comparator 44 is low.

As shown in FIG. 1 the outputs of comparators 43 and 44 are applied to And gates 51 and 52 respectively. However, these gates are only enabled when a beat pulse 15 is received, which also resets the counter 42 through Or gate 46 after a delay provided by 47. The delay is required to permit gates 51 and 52 to become enabled and possibly set one of FFs 55 and 56, depending on the outputs of the comparators, before the counter 42 is reset. This delay can be extremely short, on the order of 1 ms or less.

In operation the frst heart pulse 15 at time $t_2$, following the On or high period P of one shot 31, sets FF 38. Therefore, gate 41 is enabled and counter 42 counts the pulses at 100 pps from clock 40. When the next beat pulse 15 is received at time $t_3$ gate 35 is again enabled and provides a high output, thereby enabling gates 51 and 52. If while gates 51 and 52 are enabled the heart beat rate is between 1 bps (60 bpm) and 2 bps (120 bpm) i.e., 0.5 second $\leq (t_3 - t_2) \leq$ 1.0 second, the count in counter 42 is not less than 50 or more than 100. Since counter 23 stored a count of 100 the output of comparator 43 is low. Therefore, one of inputs to gate 51 is low and consequently it does not provide a high output which would have set FF 55. Similarly, since counter 24 stores a count of 50 and the count in counter 42 is not less than 50 the output of comparator 44 is low and therefore gate 52 does not set FF 56. With neither FF 55 nor 56 set, Or gate 58 is not enabled and therefore the alarm 60 is not activated. After a short delay provided by delay unit 47, the counter 42 is reset and starts counting pulses from clock 40 to effectively measure the time interval between the beat pulse 15 sensed at time $t_3$ and the next beat pulse assumed to be sensed at time $t_4$.

If, however, the heart beat rate is one outside the range of 60 bpm and 120 bpm one of the flip flops 55 or 56 will be set and cause the alarm 60 to be activated. For example, if the heart beat rate is 40 bpm the interval between beat pulses is 1.5 seconds. Thus, the count in counter 42 between pulses reaches 150. Consequently, the output of comparator 43 goes high and therefore when gate 51 is enabled by a beat pulse 15 its output goes high and therefore FF 55 is set. As a result, the output of Or gate 58 goes high and activates the alarm 60 to indicate an out of range condition. On the other hand if the heart beat is higher than the high limit 120 bpm e.g., 150 bpm the interval between beat pulses is only 0.4 second. Thus, the count in counter 42 will reach only a count of 40 when the gate 52 is enabled. Since the count in counter 24 is 50, i.e., higher than 40 in counter 42, the output of comparator 44 will be high and therefore gate 52 will set FF 56, which will cause Or gate 58 to activate the alarm 60. As long as either FF 55 or FF 56 is set the alarm 60 remains activated. The wearer may reset the set flip flop by momentarily depressing reset switch 57. It should be pointed out that the output of Or gate 58 may be used to activate any device which would provide the wearer with an out-of-range indication. For example, a light may be energized by the output of Or gate 58, together with or instead of activating alarm 60. Thus, numeral 60 should be regarded as representing one or more energizable devices to provide an out-of-range indication.

Figure 10:
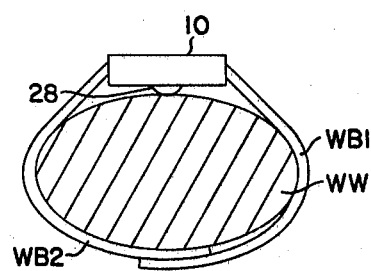
FIG. 10 represents a diagram of the monitors positioned an a wrist.

As previously pointed out, the switch 28 is used to control the supply or power from the battery 27 to the monitor's circuitry, except for the memory means, i.e., counters 23 and 24 in which the limits are stored and which are powered continuously by separate battery 26. Thus, whenever the monitor is not in use the switch 28 should be open (Off), as shown. When in use the switch is closed (On). As previously indicated, it may be of the type which closes automatically when the monitor is worn. For example, it may be a pushbutton type switch which closes upon placing the monitor on the wearer's wrist as shown in FIG. 10 wherein the wearer's wrist is shown in cross section and designated by WW, and the monitor 10 is shown secured to the wrist by wrist bands WB1 and WB2.

Figure 3:
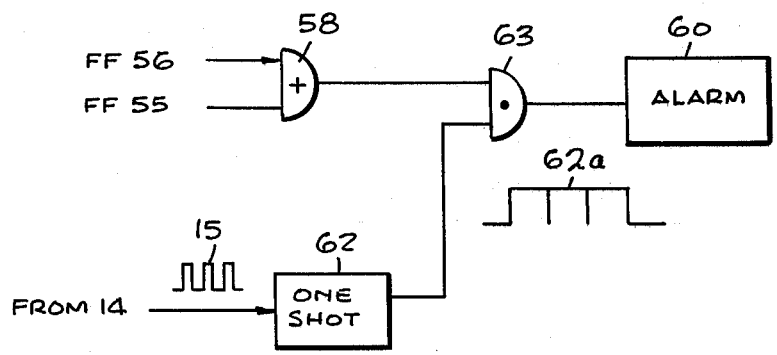
FIG. 3 is a diagram of a portion of the monitor circuitry.

When the monitor is first placed in position and switch 28 is closed, either automatically or manually, FFs 55 and 56 should be in the reset state, to prevent unintentional activation of the alarm 60. If desired a one shot (not shown) of very short time duration may be incorporated. The latter may be used to provide a resetting pulse to the flip flops whenever switch 28 closes. During use the flip flops are resettable by switch 57. After switch 28 is closed, it is desirable to insure that the alarm 60 is not activated, except due to beat pulses which correspond to heart beats, sensed by sensor 12, at a rate outside the range, defined by the stored limits. This may be achieved by incorporating in the monitor an additional one shot 62 and an And gate 63, as shown in FIG. 3.

Basically, the one shot 62 is of the resettable type and responds to each beat pulse 15, from converter 14, which drives the output of the one shot high as represented by 62a for a selected period, which is not less than the period between any two pulses 15 at the lowest expected heart beat rate. Thus, as long as heart beats are sensed, at a rate not less than the minimum expected rate, the first pulse 15 will activate the one shot 62 to provide a high output and each subsequent pulse 15 will reset the one shot 62 to maintain the output high. The high output of one shot 62 will enable gate 63 to activate alarm 60 when the output of Or gate 58 goes high. However, if heart beats are not sensed for some reasons such as due to improper alignment of the heart sensor 12, the output of one shot 62 is low, thereby disabling gate 63, so that even if switch 28 is closed and the output of Or gate 58 is high the alarm 60 is not activated.

Assuming that the minimum expected heart beat rate is 30 bpm, which corresponds to a period of 2 seconds between heart beats, the period of one shot 62 may be chosen to be slightly greater than 2 seconds, e.g., 2.1 seconds. Such an arrangement would prevent the alarm 60 from being activated, unless heart beats at a rate of at least 30 bpm are sensed.

In the foregoing described embodiment the wearer is provided only with an indication that the heart beat rate is outside the chosen range when the alarm 60 is activated. However, the wearer is not provided with an indication of his actual heart beat rate. Also, the wearer is not provided with an indication of the limits stored in counters 23 and 24. If desired, the wearer may be provided with an indication in the form of a visual display of his actual heart beat rate or either of the stored limits by the addition of some circuitry, which will be described in connection with FIG. 4.

Therein, numeral 65 represents a four-position display control switch, with positions designated OFF, LOW LIMIT, HIGH LIMIT, and SENSED RATE. Numeral 66 designates a multibit register, while numeral 67 designates a display calculator. And gates 68 and register 66 are energized only when the switch 65 is in the SENSED RATE position. Gates 68 are enabled only when each pulse 15 from converter 14 is produced. Thus, as each beat pulse is received prior to resetting the counter 42 its content is transferred to register 66 and remains stored therein until a subsequent pulse 15 is received. The outputs of register 66 when the latter is energized when switch 65 is in the SENSED RATE position are connected to a display calculator 67 through Or gates 69. When the switch 65 is in the LOW LIMIT position And gates 66a are energized to supply the count in counter 23 to calculator 67 through Or gates 69, while when switch 65 is in the HIGH LIMIT position And gates 66b are energized to supply the high limit count in counter 24 to calculator 67 through gates 69. The function of calculator 67 is to convert the count supplied thereto into a number in beats per desired unit of time, e.g., bpm, and display said number.

As should be apparent from the foregoing description, in counter 42, which is assumed to be a multibit counter, before it is reset by a delayed beat pulse 15, the count in it is related to the time interval since the preceding beat pulse. If desired the stages of counter 42 may be connected to corresponding stages of a register 66 through control gates 68. These gates are assumed to be enabled by the leading edges of the beat pulses 15. Thus, as each beat pulse is received, prior to resetting the counter 42 its content is transferred to register 66 and remains stored therein until a subsequent pulse 15 is received. The register 66 is shown connected to a display calculator 67 whose function is to convert the count in register 66 and display it as a number in beats per desired unit time, e.g., bpm.

For the foregoing description, in which the clock 40 is assumed to provide 100 pps, the required calculation is $D = (60 \times 100)/R$ where R is the supplied count in register 66, or counter 23, or counter 24 and D is the displayed number in beats per minute. Clearly, known calculator circuitry and displays, such as those employed in small pocket calculators, can be used in implementing the display calculator 67. In general, the required calculation can be expressed as $D = (T \times C)/R$, where D is the displayed heart beat rate for a period of T seconds, C represents the number of pulses per second from clock 40 and R is the supplied count.

In the particular example, when the sensed rate is selected for display, the display will be updated for every heart beat. If this update rate is found to be too high the control gates 68 may be enabled by every nth beat pulse, where n is an integer. In order to minimize the depletion of the main battery 27, the circuit shown in FIG. 4 should be connected so that register 66 and gates 68 are energized only when switch 65 is in the SENSED RATE position, gates 66a and 66b are energized only when switch 65 is in the LOW LIMIT and HIGH LIMIT position respectively, and display calculator 67 and Or gates 69 are energized whenever switch 65 is other than in the OFF position.

From the foregoing it should be appreciated that several unique advantages are realized with the monitor of the present invention. In the novel monitor the limits, which define the rate range, are transmitted into the monitor from an external unit. Thus, the wearer cannot change them unless he has access to the external unit. This is particularly significant when the potential wearer is a patient under a physician's supervision and only the physician desires to have control over the limits, depending on the patient's medical condition. Also, in the monitor of the present invention a multibit sync pattern is transmitted, ahead of the rate-limit-indicating signals, such as the 0's and 1's, hereinbefore described. Also, the transmitted 0's and 1's in the sequence are controlled to have appropriate shapes. Such an arrangement insures that only the proper transmitted binary signals, following the sync pattern, rather than noise or other signals are used to define the limits, which are stored in the monitor's memory means, such as the counters 23 and 24. Furthermore, by powering the latter with a battery, such as battery 26, which is separate from the main battery 27, used to power the rest of the monitor's circuitry, the depletion of the main battery 27 does not affect the limits' storing counters. Thus, the monitor's reliability is greatly enhanced.

In addition, in the described embodiment after the storing of the limits, the time interval between every pair of successive beat pulses 15, such as those sensed at times $t_2$ and $t_3$, $t_3$ and $t_4$, etc., is measured, to provide an indication whether the sensed heart beat rate between any of these pairs of pulses is within or outside the selected range. This is believed to be quite significant for cases in which it is important to produce an out-of-range indication, preferably as soon as the heart beat rate is outside the range, particularly when it exceeds the high limit. This may be quite important to prevent possible permanent injury to the wearer, which may result if the out-of-range indication were produced only after a relatively long period, e.g., 15 seconds during which a large number of potentially damaging high rate heart beats may occur. In another embodiment of the invention to be described hereinafter several heat beats may occur before an out-of-range indication is produced. However, therein the maximum number of heart beats which may occur before the out-of-range indication is produced is very small generally less than 10. Thus, for all practical purposes the out-of-range indication is produced practically as soon as the sensed heart beat rate is outside the range.

It should be appreciated by those familiar with circuit designs that various circuit means may be used to implement the circuitry, hereinbefore described. Therefore, the following description should be regarded as only specific examples of circuitry which may be used, rather than to limit the invention thereto. As previously explained the sync pattern and the rate-limit-indicating signals may be transmitted to the monitor by amplitude modulating a RF carrier. Attention is now directed to FIG. 5 in which one possible embodiment of circuitry, represented in FIG. 1 by unit 22, one shot 31, And gates 33 and 34 and to inverter 36 and 61, is diagrammed.

Figure 9:
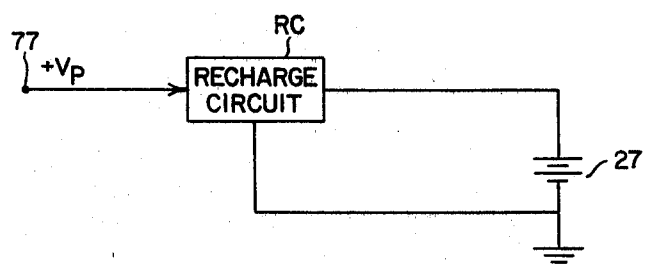
FIG. 9 is a diagram indicating an arrangement for recharging the battery.

Briefly, in FIG. 5, numeral 70 represents a receiver and decoder unit, shown including a pickup coil 72, which picks up the amplitude-modulated RF carrier (see FIG. 1a) which is transmitted from the external unit 20. The receiver and decoder unit 70 is shown to include a rectifying circuit, consisting of a diode D1 and a capacitor C1, resistors R1–R4, a transistor Q1, a Zener diode Z1, another diode D2 and two capacitors C2 and C3, connected as shown. The received RF carrier is rectified so that the demodulated signal or ripple is present at point 75. That is, thereat a voltage, e.g., +6 volts is present which is modulated above and below its average level by the binary sequence. The output on line 76 is the original binary sequence, with the lower amplitude of each bit being at ground and its upper amplitude at a selected voltage, e.g., +5 volts, as diagrammed in line $a$ of FIG. 6. The voltage at point 77, designated $+V_p$, represents the average received voltage. It may be used to power the various circuits in the monitor which are used to detect the sync pattern and receive and store the limits in the counters 23 and 24, and thereby reduce the drainage of the main battery 27. Furthermore, if desired, the voltage $+V_p$, when present at point 77, may be used to recharge the main battery 27, assuming the latter is of the rechargeable type. In FIG. 9 a recharging circuit RC, which receives the voltage $+V_p$, is shown connected across battery 27 to recharge the latter. Such recharge circuits are well known in the art. They are typically used to recharge batteries of the type used in portable devices, e.g., cassette recorders and the like.

As shown in FIG. 5 the circuitry includes a one shot 80 and an eight-stage (S1–S8) shift register 82 to which the binary output of unit 70 on line 76 is applied as an input. The output of unit 70 is also used to clock a one shot 80, whose outputs $O_1$ and $O_2$ are applied to lines 83 and 84 respectively. The output $O_2$ is the complement of $O_1$ which is used to clock the register 82.

Defining each bit period as T, as shown in FIG. 6, the one shot 80 is clocked by each low to high transition of the unit 70 output. The time constant of the one shot is $\frac{1}{2}T$, so that $O_1$ is high for the first half of each period T, as shown in FIG. 6, line $b$, and $O_2$ is high for the second half of each period T, as shown in line $c$. The shift register 82 is clocked by the high to low transition of $O_1$, such as at times $t_1$, $t_2$, $t_3$, etc. If at the time of clocking the register the input to it, i.e., the output of unit 70 on line 76 is high, a binary 1 is clocked into S1 of the register. However, if the input is low, a binary 0 is clocked into S1. From FIG. 6, lines $a$ and $b$ it should be apparent that at times $t_1$, $t_2$, $t_3$, bits 1, 0, 1 etc., are clocked into S1 of register 82. At time $t_8$ the last bit of the 8-bit sync pattern is clocked into the register. Thus, register stages S1–S8 contain the sync pattern 00101101, respectively.

As shown in FIG. 5, the outputs of stages S3, S5 and S6 and S8 are connected directly to inputs of an 8-input And gate 85 while the outputs of stages S1, S2, S4 and S7 are connected to the gate 85 through inverters 86–89 respectively. Thus, at time $t_8$, the sync pattern of 00100101, viewed from left to right is present in stages S1–S8, respectively. Consequently, all the inputs of And gate 85 are high and therefore its output on line 91 is high, thereby indicating the identification of the sync pattern. It is used to reset counters 23 and 24 (FIG. 1) to all zero counts, and to begin the memory programming or storing operation.

As shown, the circuitry also includes a JK flip flop (FF) 92 whose K input is connected to line 91 and its clock input to line 84, on which the output $O_2$ of one shot 82 is applied. Assuming that FF 92 is clocked by the positive to negative transition of each output pulse of $O_2$ (see FIG. 6, line $c$) at time $t_9$, following $t_8$, FF 92, which is assumed to have been previously set so that its Q output is high, is reset, driving its $\bar{Q}$ output high. Once FF 92 is reset, i.e., its $\bar{Q}$ output goes high on line 93, one input to each of Nand gates 94 and 95 is high.

The other input of gate 94 is applied from the output of inverter 86. Thus, each time a 0 is clocked into stage S1 the output of inverter 86 is high and therefore the output of gate 94, which is applied to one input of Nor gate 98, goes low, thereby enabling the latter. Nor gate 98 is also supplied with $O_2$. Therefore, whenever $O_2$ undergoes a high to low transition both inputs to Nor gate 98 are low or 0's and therefore its output goes high, or is a 1, which is clocked into low limit counter 23.

For example, after the sync pattern is recognized at $t_8$, and the output of And gate 85 goes high, at time $t_9$, FF 92 is reset so that line 93 goes high, enabling gate 94 (and gate 95). Then, at time $t_{10}$, the first 0 of the sequence, which represents the low limit, is clocked into S1. Since it is a 0 bit the output of inverter 86 is high and therefore the output of Nand gate 94 is low (0). Consequently, at time $t_{11}$ both inputs to Nor gate 98 are low, and a 1 is clocked into counter 23 for the first 0. Similarly, every 0 in the sequence which defines the low limit is clocked into the low limit counter 23.

It should be pointed out that when the low limit is clocked into counter 23, Nand gate 95 is effectively disabled, in turn disabling Nor gate 99. Each 0, clocked into S1, is directly applied to Nand gate 95. Thus, its output is high, thereby disabling Nor gate 99 since the latter's output will remain low (0) regardless of $O_2$ which is applied to its other input. Thus, the output of Nor gate 99 does not clock the high limit counter 24.

After all the 0's in the sequence, representing the low limit are clocked into as 1's into counter 23, the following sequence of 1's representing the high limit is received, bit by bit and clocked into S1. Due to each 1 bit the input to gate 95 from S1 is high. Thus, the output of gate 95 remains low and therefore enables Nor gate 99. Consequently, when $O_2$ goes from high to low Nor gate 99 provides a high output which clocks high limit counter 24. After all the 1's representing the high limit, are clocked into counter 24 the 0, representing the end-of-sequence bit is received. Therefore, the states of stages S1 and S2 are 0 and 1, respectively. Consequently, both inputs to Nor gate 101 are low (0) and therefore its output goes high setting FF 92. Consequently, its Q output goes high and its $\bar{Q}$ output goes low. When $\bar{Q}$ goes low it disables both gates 94 and 95 and, therefore, no additional clocking of the limit-storing counters 23 and 24 takes place. That is, their counts remain unaltered. The Q output of FF 92 is applied to one input of And gate 35 (see FIG. 1). Thus, each beat pulse 15 sets, i.e., enables the gate 35 to provide a high output, as hereinbefore described.

From the foregoing it is thus seen that the circuitry, shown in FIG. 5, is clearly adequate and reliable to receive the transmitted binary sequence which includes a sequence portion, such as the 0's representing the low limit, a sequence portion, such as 1's representing the high limit, a sync pattern, such as the 8-bit pattern, preceding both limit-indicating signals and an end bit. Only after the sync pattern is received and recognized, i.e., decoded, resulting in a high output by gate 85 on line 91, does the loading of the counters 23 and 24 with the limits start. The use of the beat pulses 15 is temporarily suspended, since gate 35 is disabled. After both limits are stored in the counters and the end bit is received, e.g., the 0 bit following the last 1 of the high-limit-sequence portion, is FF 92 set. Consequently, all additional clocking of the counters 23 and 24 is terminated, gate 35 is enabled and the regular pulse monitoring is resumed.

It should be pointed out that the limits are stored in the counters only after the sync pattern is recognized, and limit storing is terminated when the 0 sequence-end bit is detected, thus setting FF 92, which disables the gates 94 and 95 and in turn disables counter input gates 98 and 99. Thus, the stored limits are practically immune from being affected by any noise pulses. By powering the counters with a separate battery 26, once the limits are stored, they are unaffected by drainage of the main battery 27. Once a set of limits is stored in the counters it remains unaltered until a new bit sequence is received by unit 70 from the external unit 20. The new sequence is of course recognized when the sync pattern is received and decoded, i.e., is stored in the register 82, causing And gate 85 to provide a high output, which results in subsequent limit-loading-operating steps, as hereinbefore described.

If desired, the monitor may include means to transmit the limits, stored therein, to the external unit 20 in order to verify that the chosen limits were actually loaded (stored), in the counters. This may be achieved in different ways. For example, the outputs of two oscillators at different frequencies may be amplitude modulated by the sequence of bits, supplied to the two counters during limit loading. The modulated outputs of the two oscillators may then be transmitted from the monitor to the external unit 20. Since the retransmission of the limits to the external unit 20 occurs while the latter transmits the limits for storage in the monitor, the power from the received power, e.g., $+V_p$ (at point 77, FIG. 5) may be used to power the oscillators in the monitor to minimize battery drainage.

Alternatively, if desired, at any point during actual pulse monitoring, i.e., other than when limits are stored, signals, indicative of the stored limits may be transmitted to the external unit. Using the foregoing example in which it was assumed that counters 23 and 24 store counts of 100 and 50 respectively, the counts of 100 and 50 may be converted into two voltages $V_{100}$ and $V_{50}$ which correspond to counts of 100 and 50 respectively, and be transmitted to the external unit 20 wherein these voltages, i.e., $V_{100}$ and $V_{50}$ may be used to activate appropriate displays, e.g., display counters.

For explanatory purposes an arrangement for feeding back the limits being stored to the external unit 20 during limit loading, is shown in FIG. 5. Therein, an oscillator A, assumed to provide an RF carrier at one frequency $f_1$ is shown connected to a modulator-transmitter 105, which is modulated by each of the 100 pulses as they are clocked into low limit counter 23. The modulator-transmitter 105 includes a transmitting coil 106 which couples the RF carrier at $f_1$, modulated by the 100 pulses, to a pickup coil 107 in external unit 20. The coil 107 feeds a receiver-demodulator 108 tuned to $f_1$.

The output of the latter would be 100 pulses which may be used to clock a low limit display 110.

Oscillator B assumed to provide an RF carrier at $f_2$, where $f_1 \neq f_2$, is shown connected to another modulator-transmitter 112 which is fed with the 50 pulses as they are being clocked into high limit counter 24. The modulated carrier at $f_2$ is fed to a transmitting coil 113, which couples energy to a pickup coil 114 in unit 20. Coil 114 feeds a receiver-demodulator 115, tuned to $f_2$, whose output would be a sequence of 50 pulses which may be displayed in the external unit 20, for verfication as they are loaded in the monitor's counter 24.

Clearly, oscillators A and B and units 105 and 112 may be powered by the received power $+V_p$. Furthermore, if desired a single oscillator and modulator-transmitter may be used. The pulses fed to one of the counters such as 23 may be used to modulate the RF carrier to one level of modulation, e.g., 50% while those fed to the other counter (shown in 24) used to modulate the RF carrier to another level, e.g., 30%. Then in the external unit 20 these different levels of modulation may be sensed to feed the two groups of pulses, representing the two different limits, to the two displays 110 and 120.

Attention is now directed to FIG. 7, which is an example of one embodiment of circuitry in external unit 20 for generating and transmitting the limit-indicating signals and the sync pattern to the monitor, as represented by the waveform in FIG. 1a. As previously explained, the sync pattern is represented by a fixed preselected bit pattern, for example the 8-bit sequence 10110100, as viewed from left to right. It is followed by a number of 0's defining one selected limit, e.g., the lower limit, which are followed by a number of 1's, defining the other limit. The bit sequence terminates with a 0 end bit. The number of 0's and/or 1's can be varied to vary the lower and upper limits, respectively. Each bit period is the same, hereinbefore designated as T. A binary 1 is represented by a high level during the first $\frac{3}{4}$T, followed by a low level during the last $\frac{1}{4}$T. A binary 0 is represented by a high level during the first $\frac{1}{4}$T followed by a low level during the remainder $\frac{3}{4}$T.

As shown in FIG. 7 the external unit 20 is assumed to include a clock or pulse oscillator 125 which is activated when a transmit switch 126 is closed. Once activated the clock 125 provides pulses 128 to a 2-stage binary counter 130. The interval between pulses 128 is $\frac{1}{4}$T. Thus, the counter 130 is clocked at 4 times the bit rate T. The outputs of the two stages of counter 130, are designated $C_x$ and $C_y$. The four combinations of the two stages of counter 130 during each T period are represented by the truth table next to counter 130.

The circuitry includes an 8-stage shift register 135, which is initially set to store the sync pattern 10110100, as viewed from left to right, in stages S1–S8, respectively. Then as the register 135 is clocked, as will be explained hereinafter, the bits in the stages shift from left to right. The output of stage S8 is applied to two inputs $I_2$ and $I_3$ of a four-position multiplexer 136, whose other two inputs $I_1$ and $I_4$ are connected to high $(+V)$ and low (ground) levels, respectively. The output of the multiplexer on line 137 to a modulated power oscillator 140 depends on the states of $C_x$ and $C_y$ which control which of the four inputs $I_1 - I_4$ is applied to line 137, as represented in the truth table.

As shown a Nand gate 142 is connected directly to $C_x$ and $C_y$. Thus, only when $C_x$ and $C_y$ are both 00 the output of gate 142 goes high. The low to high transition of the output of gate 142 clocks register 135.

In operation the counter 130 is assumed to be initially reset to 00 count. When clock 125 is activated by closing switch 126 each pulse 128 advances the count in counter 130. The first pulse 128 drives $C_x$ to a 1. Thus, input $I_1$, which is high, is supplied by 136, via line 137 to oscillator 140. The next pulse 128 drives $C_x$ and $C_y$ to a 01 state, in which the output of 136 is its input $I_2$. Since the first sync pattern bit in S8 is a 1, i.e., high, the output of 136 is high. Similarly, the next pulse 128 drives $C_x$ and $C_y$ to state 11 in which the output of 136 is $I_3$. It is high since S8 stores a 1. Then, when the fourth pulse 128 is received $C_x$ and $C_y$ are in the state 00 in which 136 outputs $I_4$ which is low. Also, Nand gate 142 clocks the register 135 to shift the bits forward by one stage.

From the foregoing it should thus be apparent that with the above described arrangement during each bit period T during the first ¼T the output of multiplexer 136 is high, while during the last ¼T it is low, irrespective of the bit in stage S8. However, during the center half of each T period the multiplexer output is high if the bit in S8 is a 1, and is low if the bit is a 0. The output level of multiplexer 136 on line 137 modulates power oscillator 140 whose output is the modulated RF carrier, as shown in FIG. 1a, which is applied to a transmitting coil 144 for transmission to the monitor.

As shown the circuitry further includes two variable one shots 146 and 147. It is with these one shots that an operator controls to select the limits to be transmitted. One shot 146 is used to set the low limit by controlling the number of 0's which will be transmitted following the sync pattern, while one shot 147 controls the upper limit by controlling the number of 1's which will be transmitted. In operation, when switch 126 is closed it activates one shot 146 so that its output on line 149, which is applied to one shot 147, goes high. Line 149 remains high for a variable period, chosen by the operator. As long as line 149 is high the output of one shot 147 on line 150, which is the input line to stage S1 of register 135, is low. Thus, every time register 135 is clocked and line 150 is low a 0 is clocked into S1. Defining the time constant of one shot 146 as $T_L$, during which its output is high, so that the output of one shot 147 is low, it is clear that the number of 0's, clocked into the register 135 is $T_L/T$. Clearly, by changing the number of 0's which define the lower limit can be varied.

At the end of $T_L$ the output one shot 146 goes low, triggering one shot 147, to provide a high output on line 150 for a period controlled by its variable time constant, definable as $T_H$. As long as line 150 is high, 1's are clocked into the register 135. Clearly, the number of 1's which are transmitted to define the upper limit is $T_H/T$. At the end of period $T_H$ line 150 goes low so that during the next period T a 0, representing the end of the sequence or the end bit is clocked into S1. If desired, the high to low transition on line 150 may be used to activate a delay unit 152 to open switch 126 and thereby terminate the transmission operation after a delay of $xT$, where $x$ is a number sufficiently large to insure that during $xT$ all the proper bits are transmitted. Generally, $x$ should not be less than 9 to enable the eight bits in the register and the 0 end bit to be clocked into the register after line 150 goes low, to be shifted out of the register and be transmitted out of the external unit 20.

It should thus be apparent that the circuitry, shown in FIG. 7, is capable of generating and transmitting to the monitor the bit sequence, including the 8-bit sync pattern, the 0's defining the lower limit, the 1's defining the upper limit and the 0 end bit. Clearly, by varying either $T_L$ of one shot 146 and/or $T_H$ of one shot 147 the number of 0's and/or the number of 1's which define the lower and upper limits respectively may be varied in a simple and most convenient way. Each one shot may be connected to a separate dial, calibrated in beats per minute, to facilitate the control of the time constant of the one shot.

In order to reduce the size of the monitor preferably large scale integrated (LSI) circuits should be employed. To facilitate such implementation all counters and other circuits should be of the binary type, where possible. In the embodiment, shown in FIG. 1, limit counters 23 and 24 and the pulse interval counter 42 are assumed to be of the binary type. The number of bits or stages of each of these counters clearly depends on the outside range limits to be monitored and the clock rate of clock 40.

Assuming the latter's rate to be 100pps and assuming that the monitor is designed to define a low rate, down to 30 beats per minute which corresponds to 1 beat per 2 seconds, counter 42 should be one capable of counting up to 200 pulses which is achievable with an 8-bit counter, which can count up to 256. Each of counters 23 and 24 may also be an 8-bit counter. It should be appreciated that since the count in counter 42 is compared with the counts in counters 23 in comparators 43 and 44, each of the comparators should be an 8-bit comparator.

If desired, the various circuit arrangements, hereinbefore described, may be modified considerably without departing from the spirit of the invention. For example, the low and high limits, once stored in counters 23 and 24, may be used to determine whether the beat pulses 15 (FIG. 1) are received at a rate within the rate range, defined by these limits, or are outside such range, by other than performing the comparisons, as hereinbefore described in connection with FIG. 1. Attention is now directed to FIG. 8 wherein another possible partial embodiment of the monitor is diagrammed. With such an arrangement the need for two multistage comparators, such as comparators 43 and 44 is eliminated, at the price of some additional circuit components. In FIG. 8, elements like those previously described, and performing similar functions, are designated by like numerals.

The circuitry in FIG. 8 will be described in connection with a monitor in which the lowest low limit which may be set is one corresponding to a time interval between beat pulses 15 of 2.049 seconds, which in terms of beats per second is 60/2.049 = 29.2 bpm. For explanatory purposes the lowest low limit will be assumed to be 30 bpm corresponding to 1 beat per 2 seconds. Each of the limit counters 23 and 24 is assumed to be an 11-stage binary counter, capable of counting up to 2048, (0–2047) pulses. When this count is exceeded its last stage undergoes a high to low transition. In FIG. 8 output line 161 of counter 23 is shown connected to the clock input of a D-type flip flop 162 through an inverter 163. When the count in counter 23 exceeds 2048 line 161 goes from high to low and consequently, the output of inverter 163 goes from low to high, clocking FF 162. Since FF 162 is a D-type FF with its D input at ground (low or 0), when clocked its $\bar{Q}$ output on line 162a is high.

Similarly, output line 164 of counter 24 goes from high to low when the count in counter 24 exceeds 2048, causing the output of inverter 165 to go from low to high and thereby clock D-type FF 166 so that its Q output on line 166a is low, since its D input is low (ground). The Q and Q̄ outputs of FFs 166 and 162 respectively are connected to a Nor gate 167, whose output is applied to the D input of D-type FF 168. The Q output of the latter on line 169 is connected to the alarm 60.

The circuitry further includes an input JF-type FF 170 which is clocked by the beat pulses 15 from converter 14 (FIG. 1). The Q output of FF 170 on line 171 is applied to the clock input of FF 168 and to the set (S) input of each of FFs 162 and 166. FFs 162 and 166 are set and FF 168 is clocked by the low to high transition on line 171 as indicated by arrow 172 on waveform 173. Each of these flip flops is assumed to provide a high (1) Q output when set. Thus, when FF 162 is set its Q output is high (1) and its Q̄ output is low (0).

As will be pointed out hereinafter, the counters 23 and 24 which are loaded with limits (counts), and are clocked when line 171 first goes low, so that if the heart beat rate is within the range defined by the limits, FF 166 is clocked and FF 162 is not clocked before line 171 goes high. Therefore, lines 166a and 162a are both low and the output of Nor gate 167 is therefore high, so that when FF 168 is clocked line 169 is high and the alarm 60 is not activated. If, however, the heart beat rate is higher than the upper limit, set in counter 24, FF 166 is not clocked before line 171 goes high. Therefore, line 166a is high and therefore the output of Nor gate 167 is low when FF 167 is clocked. Consequently, line 169 goes low and the alarm 60 is activated. On the other hand, if the heart beat rate is below the lower limit, set in counter 23, FF 162 is clocked before line 171 goes high. Therefore, line 162a goes high, so that when FF 168 is clocked the output of Nor gate 167 is low and as a result line 169 goes low, activating alarm 60.

As shown in FIG. 8 the Q̄ output of FF 170 on line 175 is converted to the reset (R) input of a D-type FF 176, whose Q output on line 178 is applied to the K input of FF 170. The set (S) input of each of FFs 170 and 176 is connected to the Q output of FF 92 via line 93 (see FIG. 5). Thus, during limit loading or programming, since line 93 is high, both FF 170 and FF 176 are set (lines 171 and 178 are high) and are held in that state until limit loading is completed.

The circuitry further includes a multibit counter 180 which is clocked by pulses from an oscillator 182. For explanatory purposes the latter is assumed to provide pulses at a rate of 2 KHz, so that the rate of output pulses from the first stage of counter 180 on line 183 is 1 KHz. The counter 180 is assumed to count up to 4096 and when exceeding this count is reset so that the output of its last stage undergoes a high to low transition, produced on line 185, which is connected through inverter 187 to the clock input of FF 176. When the latter is clocked since its D input is connected to +V its Q output is high. However, when FF 176 is reset its Q output on line 178 undergoes a high to low transition. Line 178 is connected to the reset input of counter 180. When line 178 undergoes a low to high transition the counter 180 is reset and prevented from counting the pulses from oscillator 182 until line 178 undergoes a high to low transition. In addition, a 2-position switch 190, shown for explanatory purposes as a mechanical switch, is included. During programming when line 93 is high switch 190 is in the position as shown. Thus, the limit-indicating pulses are clocked into the counters 23 and 24, as previously explained. However, after programming when FF 92 is set and line 93 is low switch 190 connects line 183 to gates 98 and 99 so that the pulses from the first stage of counter 180 at 1 KHz are clocked into the counters 23 and 24.

The operation of the circuitry may best be explained with a specific example. Let it be assumed that the low limit is chosen to be 30 bpm, which corresponds to a 2 second interval between pulses. Since the maximum count in counter 23 is 2048 and is clockable by pulses on line 183 at 1 KHz during programming the counter 23 is clocked to a count of 2048 − 2(1000) = 48. Let the selected upper or high limit be assumed to be 150 bpm, corresponding to an interval between beat pulses of 0.4 second. During programming counter 24 is clocked to a count of 2048 − 0.4(1000) = 2048 − 400 = 1648. As previously explained during programming both FF 170 and FF 176 are held in a set state and therefore lines 171 and 178 are high. FF 170 does not change state during programming irrespective of the clocking beat pulses 15. Also, since line 178 is high counter 180 is an all 0 or reset state.

After programming is completed, i.e., line 93 goes low. The first beat pulse 15 following programming, such as $t_x$ (see waveform 173) clocks FF 170 which toggles (since both J and K are high), i.e., switches to its reset state so that line 171 goes low and line 175 goes high. When line 175 goes higher it resets FF 176. Consequently, line 178 goes low. The high to low transition on line 178 enables counter 180 to count the 2 KHz pulses from oscillator 182. However, the pulses on line 183, which are fed to counters 23 and 24 through switch 190 and gates 98 and 99, are at a 1 KHz rate. Thus, the count in counter 23 which was programmed to 48 increments is at a 1 KHz rate. Similarly, the count in counter 24, programmed to 1648, increments at the same rate.

When the second pulse 15 arrives such as at time $t_x$ it clocks FF 170 so that line 171 goes high thereby setting FF 162 and FF 166 and clocking FF 168. However, when FF 168 is clocked, whether or not alarm 60 is activated depends on the time which elapsed between the first pulse 15 (at $t_x$) which reset FF 170 so that line 171 went low, and the second pulse 15 (at time $t_y$) which sets FF 170 causing line 171 to go high, and thereby clock FF 168.

For the particular example for a range of 30 bpm to 150 bpm counters 23 and 24 were programmed to contain counts of 48 and 1648 respectively. If the interval between the first and second pulses 15, i.e., $t_y - t_x$ is not less than 0.400 second, corresponding to a rate not greater than 150 bpm, and is not greater than 2.000 seconds, corresponding to a rate of not less than 30 bpm, then before the second pulse 15 is received at time $t_y$, FF 166 is clocked, while FF 162 is not clocked, so that it remains set. Therefore, when FF 168 is clocked, since both inputs to Nor gate 167 are low, its output is high and therefore line 169 is high, resulting in the alarm 60 not being activated. However, if the heart beat rate is greater than the upper limit of 150 bpm, e.g., 180 bpm so that the interval ($t_y - t_x$) between the first and second pulses 15 is only 0.333 second, only 333 pulses are clocked into counter 24 which was set to a count of 1648. Consequently, its count reaches 1648 + 333 = 1981 when the second pulse 15 is received at time $t_y$ and therefore FF 166 is not clocked. Consequently, line 166a is high, and the output of Nor gate 167 is low when FF 168 is clocked. As a result, alarm 60 is activated to indicate an out-of-range condition.

On the other hand, if the heart beat rate is below the set low limit of 30 bpm (represented by the count of 48 set in counter 23), e.g., 20 bpm, the time interval $t_y - t_x$ between the first and second pulses 15 is 3 seconds. Consequently, before the second pulse 15 is received at time $t_y$ more than 2000 pulses have been clocked into counter 24, and it in turn causes FF 162 to be clocked, so that line 162a goes high. Consequently, when the second pulse 15 is received at time $t_y$, the output of Nor gate 167 is low, so that when FF 168 is clocked line 169 is low activating alarm 60 to indicate the out-of-range condition.

As shown in FIG. 8 and as previously explained when counter 180 reaches a count of 4096 (such as at time $t_z$), which corresponds to 2048 pulses from its first stage on line 183, FF 176 is clocked so that its Q output on line 178 goes high, resetting the count in counter 180 and stopping the counting of the pulses from oscillator 182, until line 178 goes low once more. Since each of counters 23 and 24 are capable of counting up to 2048, the original limits stored therein, e.g., 48 and 1648 respectively, are re-established therein.

It should be pointed out that after the first pulse 15 following limits' loading or programming, when line 171 goes low (such as at $t_x$) the J input to FF 170 is high and the K input is low. Line 171 remains high irrespective of the appearance of additional pulses 15 at the clock input of FF 170, as long as the K input is low. However, once line 178 goes high, such as at time $t_z$, the K input of FF 170 is high so that when the next pulse 15 is received it clocks FF 170, resetting it, which initiates a second compare cycle.

For the particular example in which counter 180 is clocked by 4096 pulses until it clocks FF 176, which corresponds to clocking counters 23 and 24 with 2048 pulses, the number of heart beats or pulses 15 between updates (compare cycles) is as shown in the following table:

| RATE (bpm) | INTERVAL BETWEEN HEART BEATS (PULSES 15) | TIME BETWEEN UPDATES | NO. OF HEART BEATS (PULSES 15) BETWEEN UPDATES |
|---|---|---|---|
| 30 | 2000 ms | 4 sec. | 2 |
| 60 | 1000 | 3 | 3 |
| 100 | 600 | 2.4 | 4 |
| 120 | 500 | 2.5 | 5 |
| 200 | 300 | 2.1 | 7 |

From the foregoing it should thus be appreciated that in the arrangement, shown in FIG. 8, the FFs 162 and 166 effectively replace the multistage or multibit comparators 43 and 44, respectively, shown in FIG. 1. However, the saving in the number of stages, needed to determine whether the heart beat rate is within or outside the range, defined by the limits, is partially reduced by the need of FFs 170 and 176.

It should be appreciated by those familiar with the art that, if desired, the limits, stored in the counters 23 and 24 in the arrangement shown in FIG. 8, may be retransmitted to the external unit 20, for verification, in a manner similar to the arrangement shown in FIG. 5. For example, during one compare cycle modulator transmitter 105 (see FIG. 5) may be enabled from the start of the compare cycle $t_x$ until counter 23 reaches a full count and line 161 goes high, thereby enabling the modulator transmitter 105 to transmit to the external unit 20 a number of pulses corresponding to the difference between the maximum count which can be stored in counter 23, (2048) and the previously set low limit therein, such as for example 48, i.e., 2000 pulses, which would indicate in the external unit 20 that the proper limit, namely 48 pulses, were stored in the counter 25. Then, during a subsequent compare cycle modulator transmitter 112 may be enabled to transmit the pulses being supplied to the high limit counter 24 until the latter reaches a full count, namely its output line 164 goes high. In the particular example in which it was assumed that the counter 24 was prestored with a count of 1648 pulses, 400 pulses would be transmitted to the external unit 20 which when displayed would indicate that the proper high limit, represented by 1648 pulses, previously programmed into counter 24, have been properly stored therein. Clearly, other arrangements may be employed to transmit to the external unit 20 the limits stored in the counters 23 and 24, for verification purposes.

Although particular embodiments of the invention have been described and illustrated herein, it is recognized that modifications and variations may readily occur to those skilled in the art and consequently, it is intended that the claims be interpreted to cover such modifications and equivalents.

The embodiments of the invention in which an exclusive property or privilege is claimed are defined as follows:

1. A system for monitoring heart beats of a subject, comprising:
a heart beat monitor including heart beat sensing means for sensing the subject heart beat and for providing pulses corresponding thereto, first means including receiver means for receiving signals transmitted to said monitor from a source external thereto, said signals including signals defining at least a selected upper limit of heart beat rate, and memory means for storing said upper rate limit defining signals, received by said received means, circuit means responsive to said pulses for comparing their rate with said rate upper limit, stored in said memory means, and for providing an indication to said subject when the rate of said pulses exceeds the rate upper limit, and a power source means for powering at least said circuit means; and
means external to said monitor for transmitting signals to said receiver means in said monitor, said signals including signals defining at least said selected rate upper limit, said external means including controllable variable means for controlling the rate upper limit defined by said signals.

2. The system as described in claim 1 wherein said external means include means for transmitting a preselected sequence of signals, defining a sync pattern, prior to transmitting signals defining at least said selected rate upper limit, and said receiver means in said monitor include means for identifying said sync pattern and for enabling said memory means to store the signals defining said rate upper limit only after said sync pattern is identified.

3. The system as described in claim 2 wherein said external means include means for transmitting following each sync pattern two sets of signals, one of which defines said selected rate upper limit and a one set defining a selected rate lower limit, the two rate limits defining a heart beat range, said memory means in said monitor include separate means for storing said rate upper and lower limits received from said receive means after the identification of said sync pattern, and said monitor's circuit means include means for providing said indication to said subject when the heart beat range thereof is outside said heart beat rate range.

4. The system as described in claim 1 wherein said power source means includes a first power source for powering at least said circuit means and a second separate power source for powering only said memory means.

5. The system as described in claim 4 wherein said external means include means for transmitting a preselected sequence of signals defining a sync pattern prior to transmitting signals defining at least said selected upper rate limit, and said receiver means in said monitor includes means for identifying said sync pattern and for enabling said memory means to store the signals defining said upper rate limit only after said sync pattern was identified.

6. The system as described in claim 5 wherein said external means includes means for transmitting following each sync pattern two sets of signals one of which defines said selected upper limit and a one set defining a selected lower rate limit, the two limits defining a heart beat rate range, said memory means in said monitor include separate means for storing said upper and lower rate limits received from said receiver means after the identification of said sync pattern, and said monitor's circuit means include means for providing said indication to said subject when the heart beat rate thereof is outside said heart beat rate range.

7. The system as described in claim 1 wherein said monitor includes second means for producing a visual display of the rate per a selected unit of time at which pulses were sensed by said sensing means.

8. The system as described in claim 7 wherein said second means are powerable by said power source and include subject-controlled switch means for controlling the powering of said second means by said power source means.

9. The system as described in claim 8 wherein said power source means includes a first power source for powering at least said circuit means and a second separate power source for powering only said memory means.

10. The system as described in claim 9 wherein at least said first power source is a battery rechargeable by power received by said receiver means when signals are transmitted thereto from said external source.

11. The system as described in claim 1 wherein said system further includes means in said monitor for transmitting to said external means signals representing at least the limit stored in said memory means, and means in the external means for receiving the signals transmitted thereto and for providing an indication of the limit represented by said received signals.

12. The system as described in claim 1 wherein said monitor further includes selectively energizable means for providing an indication of the limit stored in said memory means.

13. A system for monitoring heart beats of a subject comprising:
a heart beat monitor including, heart beat sensing means for sensing the subject heart beats and for producing a pulse corresponding to each sensed heart beat, receiver means adapted to receive signals transmitted thereto from external means and for identifying in said received signals a first set of signals defining a rate high limit and a second set of signals defining a rate low limit, memory means coupled to said receiver means for separately storing therein the high and low limits, said limits defining a heart beat rate range, and circuit means responsive to the pulses corresponding to the sensed heart beats and including indication means for providing an indication when the rate of the sensed heart beats is outside the rate range defined by said stored limits, and power means for powering at least said circuit means; and
external means for transmitting to said receiver means signals including said first and second sets of signals defining said limits, said external means including means for separately selectively varying the signals in each set to vary the rate limit defined thereby.

14. The system as described in claim 13 wherein said monitor further includes selectively energizable means for displaying the sensed heart beat rate of the subject.

15. The system as described in claim 13 wherein said system further includes means in said monitor for transmitting to said external means signals corresponding to the high and low limits stored in said memory means, and means in said external means for receiving and utilizing the limits' indicating signals, transmitted thereto, to provide indications corresponding to the limits stored in the memory means of said monitor.

16. The system as described in claim 13 wherein said monitor's power means comprises a rechargeable battery, rechargeable by power from said receiver means when signals are transmitted thereto from said external means.

17. The system as described in claim 13 wherein said power means includes a separate power source for powering said memory means.

18. The system as described in claim 13 wherein said monitor includes selectively energizable means for providing at least one rate indication corresponding to at least one of the limits stored in said memory means.

19. The system as described in claim 13 wherein said external means include means for generating and transmitting a preselected sequence of signals defining a sync pattern prior to transmitting said first and second sets of signals, and said receiver means include means for identifying said sync pattern and for enabling said memory means to store said high and low limits only after said sync pattern is identified.

20. The system as described in claim 19 wherein said monitor further includes selectively energizable means for displaying the sensed heart beat rate of said subject.

21. The system as described in claim 20 wherein said system further includes means in said monitor for transmitting to said external means signals corresponding to the high and low limits stored in said memory means, and means in said external means for receiving and utilizing the limits' indicating signals transmitted thereto to provide indications corresponding to the limits stored in the memory means of said monitor.

22. The system as described in claim 21 wherein said power means includes a separate power source for powering said memory means.

23. The system as described in claim 21 wherein said monitor includes selectively energizable means for providing at least one rate indication corresponding to at least one of the limits stored in said memory means.

24. The system as described in claim 21 wherein said power means includes first power means for powering said memory means and second power means for powering at least said circuit means exclusive of said memory means, and said monitor includes selectively controllable means for providing a visual indication to said subject of the limits in said memory means.

25. The system as described in claim 13 further including means for inhibiting said indication means from providing said indication when the rate of the heart beat sensed by said sensing means is below a preselected rate, which is lower than the rate defined by said low limit.

26. The system as described in claim 13 wherein said monitor is of the wrist type, and includes switch means for connecting said power means to said circuit means only when said monitor is placed on the subject's wrist.

27. The system as described in claim 24 further including means for inhibiting said indication means from providing said indication when the rate of the heart beat sensed by said sensing means is below a preselected rate, which is lower than the rate defined by said low limit.

28. A system for monitoring heart beats of a subject comprising:
    heart beat sensing means for sensing the subject's heart beats and for producing a pulse corresponding to each sensed heart beat,
    memory means for storing variably selected high and low limits which define a rate range;
    circuit means coupled to said memory means and to said sensing means for providing first and second signals when the sensed heart beats are at rates outside and within said range, respectively;
    power means for powering at least said circuit means;
    output means coupled to said circuit means for providing an out-of range indication when said circuit means provides said first signal; and
    display means for controllably displaying an indication representing any of the rate of the sensed heart beats or one of said stored limits,
    said system further including external means for transmitting signals representing said high and low limits, and further including receiver means, coupled to said memory means, for receiving said transmitted signals and for storing the high and low limits, represented by the received signals, in said memory means.

29. The system as described in claim 28 wherein said system further includes means for transmitting to said external means signals indicative of the limits stored in said memory means.

30. The system as described in claim 28 wherein said sensing means, said memory means, said circuit means, said power means, said output means and said display means are within a monitor housing, attachable to a wrist of said subject, and including output control means for inhibiting said output means from providing said out-of-range indication in response to said first signal from said circuit means when the rate of the sensed heart beats is below a preselected rate which is lower than the rate defined by said low limit.

31. The system as described in claim 30 further including in said housing switch means for automatically disconnecting at least said circuit means from said power means when said housing is not attached to the subject's wrist.

* * * * *